United States Patent
Ehrhorn

(10) Patent No.: US 9,651,293 B2
(45) Date of Patent: May 16, 2017

(54) COOLED STORING SYSTEM FOR PHOTO CATALYTIC DECOMPOSITION OF ETHYLENE

(75) Inventor: Kristian Ehrhorn, Odense S (DK)

(73) Assignee: KJAERULF PEDERSEN A/S, Taastrup (DK)

( * ) Notice: Subject to any disclaimer, the term of this patent is extended or adjusted under 35 U.S.C. 154(b) by 267 days.

(21) Appl. No.: 14/118,089

(22) PCT Filed: May 16, 2011

(86) PCT No.: PCT/DK2011/050164
§ 371 (c)(1),
(2), (4) Date: Nov. 15, 2013

(87) PCT Pub. No.: WO2012/155907
PCT Pub. Date: Nov. 22, 2012

(65) Prior Publication Data
US 2014/0123688 A1    May 8, 2014

(51) Int. Cl.
F25D 17/04       (2006.01)
A23B 7/152      (2006.01)
A23L 3/3445    (2006.01)
A61L 9/20        (2006.01)
F24F 3/16        (2006.01)

(52) U.S. Cl.
CPC ............ F25D 17/042 (2013.01); A23B 7/152 (2013.01); A23L 3/3445 (2013.01); A61L 9/205 (2013.01); B01D 2255/802 (2013.01); B01D 2257/7022 (2013.01); B01D 2259/804 (2013.01); F24F 2003/1667 (2013.01); F25D 2317/0417 (2013.01)

(58) Field of Classification Search
CPC ...... A23B 7/152; A23L 3/3445; F25D 17/042
See application file for complete search history.

(56) References Cited

U.S. PATENT DOCUMENTS

| | | | |
|---|---|---|---|
| 5,865,959 A * | 2/1999 | Meinzer et al. | 204/157.3 |
| 6,182,461 B1 * | 2/2001 | Washburn et al. | 62/264 |
| 6,254,997 B1 * | 7/2001 | Rettig et al. | 428/553 |
| 7,951,327 B2 * | 5/2011 | Reisfeld et al. | 422/24 |
| 2005/0214533 A1 * | 9/2005 | Shimosaki et al. | 428/375 |
| 2008/0159910 A1 * | 7/2008 | Dick et al. | 422/40 |
| 2008/0314062 A1 * | 12/2008 | Ritchey | 62/291 |

FOREIGN PATENT DOCUMENTS

| | | | | |
|---|---|---|---|---|
| CN | 201407761 Y | | 2/2010 | |
| JP | 2006038355 A | * | 2/2006 | ............... F24F 1/00 |
| KR | 10-2005-0047066 A | | 5/2005 | |
| WO | 2004/065857 A1 | | 8/2004 | |
| WO | 2007/012202 A1 | | 2/2007 | |
| WO | 2010/136563 A1 | | 12/2010 | |

* cited by examiner

*Primary Examiner* — Orlando E Aviles Bosques
*Assistant Examiner* — Antonio R Febles
(74) *Attorney, Agent, or Firm* — Nath, Goldberg & Meyer; Jerald L. Meyer

(57) ABSTRACT

A cooled storing system for photo catalytic decomposition of ethylene is a reefer container or a refrigerator with a cooling unit including an evaporator, the surface of which is at least partly coated in $TiO_2$. A UV-source is arranged so that light emitted therefrom falls on the surface provided with $TiO_2$, whereby an active surface for photo catalysis is provided. When in use, an airflow created inside the system passes over the photocatalytic surface permitting decomposition of organic compounds such as ethylene present therein.

12 Claims, 1 Drawing Sheet

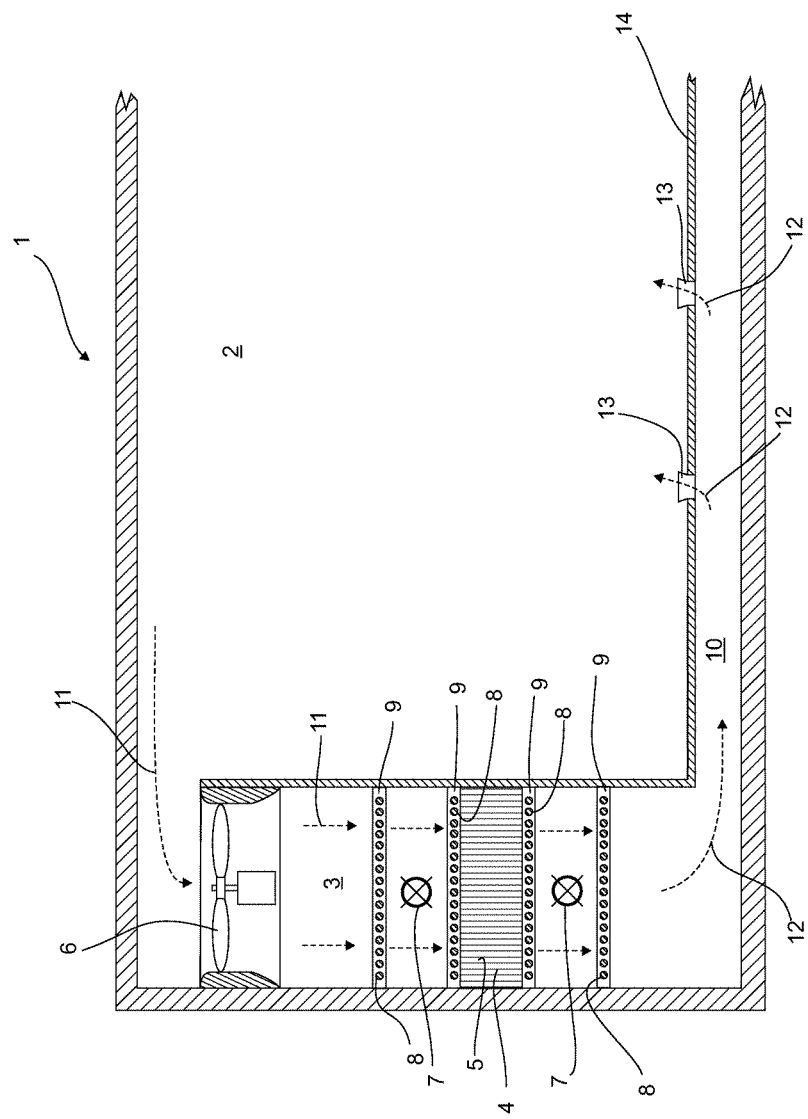

COOLED STORING SYSTEM FOR PHOTO CATALYTIC DECOMPOSITION OF ETHYLENE

FIELD OF INVENTION

The invention relates to a cooled storing system for photo-catalytic decomposition of organic compounds, particularly, it relates to a cooled storing system for decomposition of ethylene.

The invention further relates to a method for cleaning of air contained in a cooled storing system by photo-catalytic decomposition of organic compounds contained in the cooled storing system.

BACKGROUND

Ethylene concentrations more than 10 ppbv (part per billion volume) may have an adverse influence on the freshness and stock life time of perishable produce like fruit, vegetables as well as flowers and living plants. The produce may emit ethylene when it ripens, which may influence other produce in the vicinity leading to decay and reduced stock life during storage or shipping. This is the cause of a great amount of waste of produce that has become unmarketable, which is both a great environmental and economic challenge. Therefore, there is a demand for systems which effectively and economically profitably can reduce and/or remove ethylene or other organic compounds polluting the environment in storing and/or transport systems for such produce, such as e.g. reefer containers and refrigerators with controlled internal atmospheres.

Known methods of ethylene removal are ventilation, scrubbing in potassium permanganate scrubbers, and chemical reactions using ozone. Adequate ventilation may be unacceptable, because it may influence other control parameters of the controlled internal atmosphere, such as e.g. temperature, humidity, $CO_2$ and $O_2$ and will increase energy consumption in cooled and temperature-controlled environments. Scrubbing with potassium permanganate is taking up space and needs service and renewal of the used potassium permanganate. Chemical reactions with ozone require ozone generators for supplying ozone and further require decomposition of unreacted ozone. The production and subsequent removal of excess ozone constitutes an undesirable waste of resources. Further, reefer containers and refrigerators have fixed dimensions. Accordingly, any space-requiring devices for cleaning the air and/or surfaces of the storing system will influence the storage capacity in a negative way. Thus, there is a need for a more space- and energy-efficient and cost-effective method for decomposition of organic compounds in cooled storing systems.

Photo catalytic activity is the ability of a material to create an electron hole pair as a result of exposure to ultraviolet radiation. The resulting free-radicals are very efficient oxidizers of organic matter.

The use of bandgab semiconductors such as $TiO_2$, ZnO, $ZrO_2$, CdS, etc. and their various modified forms as photo catalysts is well known in the prior art. Photo catalytic activity in $TiO_2$ has been extensively studied because of its potential use in sterilization, sanitation, and remediation applications.

Two crystalline forms of $TiO_2$ have photo catalytic activity, anatase and rutile. Anatase has a band gap of 3.2 eV and for rutile it is 3.0 eV. Anatase crystalline form has been found to be the most active and is readily excited upon exposure to near UV radiation. The action spectrum for anatase shows a sharp decrease in activity above about 385 nm with optimum wavelengths of approximately 254 nm producing electron/hole ($e^-/h^+$) pairs on the semiconductor surface.

The photo catalytic process includes chemical steps that produce reactive species. The steps include formation of i.a. the following species: hydroxyl radical, hydrogen peroxide, superoxide, conduction band electron, and valence band hole.

The recombination of $e^-/h^+$ pairs has the resulting effect of reducing the process quantum efficiency. The recombination can occur either between the energy bands or on the semiconductor surface.

It has long been recognized that certain materials such as noble metals (e.g. Pt, Pd, Au and Ag) and some metal oxides (e.g. $RuO_2$, $WO_3$, and $SiO_2$) facilitate electron transfer and prolong the length of time electrons and holes remain segregated. The electrons and holes act as strong reducing and oxidizing agents that cause breakdown of the target compounds (ethylene, formaldehyde and ozone etc.) via formation of active radicals on the photo-catalyst surface. The photo-catalytic process is dependent on water i.e. from the humidity in the air.

Electron-Hole Pair Formation:

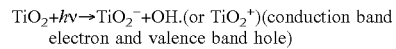
$TiO_2 + h\nu \rightarrow TiO_2^- + OH.(or\ TiO_2^+)$(conduction band electron and valence band hole)

Oxidation of Organic Compounds:

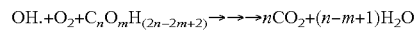
$OH. + O_2 + C_nO_mH_{(2n-2m+2)} \rightarrow \rightarrow \rightarrow nCO_2 + (n-m+1)H_2O$ Oxidation of Ethylene:

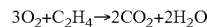
$3O_2 + C_2H_4 \rightarrow 2CO_2 + 2H_2O$

It has been described in CN201312536U to use photo catalysis for ethylene removal in refrigerated containers. However, this system is arranged in a dedicated and space demanding reaction tank inside the container, thus reducing the storage capacity and further requiring an increased amount of energy to circulate air into the reaction tank.

It is a first object of the present invention to provide a cooled storing system for photo catalytic decomposition of ethylene that is space- and energy-efficient and/or cost-effective.

It is another object of the present invention to provide a cooled storing system for photo catalytic decomposition of ethylene that is simple and easily maintained.

It is a further object of the present invention to provide a cooled storing system for photo catalytic decomposition of ethylene, wherein the photo catalytic surfaces are substantially self-cleaning.

It is a further object of the present invention to provide a method for photo-catalytic decomposition of organic compounds contained in a cooled storing system, which method is space- and energy-efficient and/or cost-effective.

BRIEF DISCLOSURE OF THE INVENTION

In the experimental development leading to the present invention, the inventor found that to be able to better utilize the space of a storing system for the actual storing of produce, advantageously, the space needed for equipment for controlling and/or reducing the ethylene concentration inside the storing system must be reduced. The inventor surprisingly found that instead of placing a dedicated and space demanding reaction chamber for ethylene decomposition inside the storage room, the existing surfaces inside a cooled storing system comprising a cooling unit could be used for photo catalytic decomposition of ethylene or other organic compounds. More specifically, the inventor found that it is possible to coat the existing surfaces of the cooled storing system with $TiO_2$ and provide UV light sources in the vicinity of the treated surfaces. The inventor surprisingly found that the surface of the evaporator of the cooling system was excellent for this purpose, optionally supplemented by coating with $TiO_2$ of other existing or added surfaces. This is particularly energy efficient as the air is already circulated over the evaporator and thus, does not need to be circulated through a separate reaction tank as in the prior art. Moreover, this is an efficient use of space.

Accordingly, the invention relates to a cooled storing system for photo-catalytic decomposition of ethylene comprising a cooling unit, said cooling unit comprising an evaporator with at least one surface, wherein said cooled storing system further comprises means for providing an airflow inside said system, at least one UV-source, and wherein $TiO_2$ is at least provided on part of said at least one surface of the evaporator and wherein said at least one UV-source is arranged so that light emitted therefrom falls on said surface provided with $TiO_2$.

Further, the invention relates to a method for cleaning of air inside a cooled storing system said method comprising photo-catalytic decomposition of organic compounds contained in a cooled storing system provided with a cooling unit, said cooling unit comprising an evaporator with at least one surface said method comprising the following step:

a) providing an airstream containing organic compounds;
b) providing means for photo catalysis, said means comprising at least one UV-source and $TiO_2$ provided on at least part of said at least one surface of the evaporator, and wherein said at least one UV-source is arranged so that light emitted therefrom falls on said surface provided with $TiO_2$;
c) passing the airstream containing organic compounds over the surface provided with $TiO_2$ and UV light.

DEFINITIONS

"Active surface" as used herein refers to surfaces coated with $TiO_2$ and exposed to UV-light.

Ethylene is $C_2H_4$.

DETAILED DESCRIPTION OF THE INVENTION

It was found that coating of existing surfaces inside a cooled storing system such as a reefer container or a refrigerator with $TiO_2$ and exposing these coated surfaces to UV-light was very efficient for decomposition of ethylene and other organic compounds, while at the same time being a space and energy efficient solution. Another advantage of this solution is that the coated surfaces reveal disinfecting and self-cleaning properties under exposure to UV emission. That is, organic compounds and contaminants such as e.g. bacteria that contaminate the surfaces of the cooled storage system are decomposed by the photo catalytic properties of the active surfaces. This is a particular advantage with respect to the surfaces of the evaporator where contaminants may cause a reduced cooling capacity over time. By making this surface active, the other-wise required regular cleaning may be avoided or at least the cleaning frequency may be radically reduced. Another advantage is that this solution is inexpensive to produce and has a low maintenance cost compared to prior art solutions.

Accordingly, the invention relates in one embodiment to a cooled storing system for photo-catalytic decomposition of ethylene, comprising a cooling unit, said cooling unit comprising an evaporator with at least one surface, wherein said cooled storing system further comprises means for providing an airflow inside said system, at least one UV-source, and wherein $TiO_2$ is at least provided on part of said at least one surface of the evaporator and wherein said at least one UV-source is arranged so that light emitted therefrom falls on said surface provided with $TiO_2$.

Hereby, a system is provided wherein the existing surface of the evaporator is used for photo-catalytic decomposition of ethylene in cooled storing systems. The evaporator preferably has a large surface area, and thus, the surface area for photo-catalytic decomposition of ethylene is likewise large, which is an advantage because the ethylene must be in close contact with the active surface to be decomposed by photo catalysis. Accordingly, the larger the active surface area, the higher proportion of ethylene comprised in the air is decomposed per each round of air exchange.

The means for providing airflow may be any suitable device such as e.g. a fan or air pump or the like. The air of the cooled storing system is driven over the evaporator for the purpose of cooling the air, but at the same time ethylene and/or other organic compounds comprised in the air is decomposed by a photo catalytic reaction when the compound comes into contact with the UV-illuminated active surface, i.e. the surfaces coated with $TiO_2$ that is exposed to UV radiation from the UV-light source. Thus, the present invention takes advantage of existing means for reducing the temperature in the storing system, i.e. means for providing airflow and the evaporator. Accordingly, the decomposition of ethylene or other organic compounds comprised in the air of the cooled storing system does not require further energy as the flow resistance in the system has not been increased.

The evaporator may be partly coated on one or more of the surfaces. In one embodiment, it is coated substantially on the entire surface however; in another embodiment it is only coated on part of the surfaces. The coating is preferably so thin that its influence on the cooling capacity of the system is insignificant.

During the cause of the present invention, the inventors found that a coating thickness of between 10 nm and 300 μm provides the best balance between the need for catalysis of the organic compounds and the need for minimal influence on the cooling capacity. In one embodiment the $TiO_2$ coating is provided in a thickness of between 100 nm and 30 μm. In another embodiment the coating is provided in a thickness of between 500 nm and 10 μm, such as 0.6, 0.7, 0.8, 0.9, 1.0, 1.1, 1.2, 1.3, 1.4, 1.5, 1.6, 1.7, 1.8, 1.9 or 2.0 μm. In a preferred embodiment, the coating has a thickness of about 1 μm.

The evaporator is part of a cooling unit and is connected to a condenser and a compressor, that are both preferably arranged externally to the controlled internal atmosphere, i.e. preferably on the external side of the cooled storing system.

The UV-source may be one or more UV-light tubes. The light sources are to be arranged so that light emitted therefrom falls on the $TiO_2$ coated surface, whereby the active surface is obtained. Accordingly, the light source may be situated on any side of the evaporator, i.e. e.g. above and/or below and/or to one or the other side of the evaporator.

In one embodiment the light source is an Hg-light tube. The action spectrum for anatase $TiO_2$ shows a sharp decrease in activity above about 385 nm with optimum wavelengths of approximately 254 nm producing electron/ hole ($e^-/h^+$) pairs on the semiconductor surface. Accordingly, the wavelength of the UV-light source is between 250-385 nm. Preferably it is 254 nm.

Accordingly, a system is provided that decomposes by photo catalysis almost all organic matter coming into contact with its active surfaces, and that breaks down $C_2H_4$ without additional use of dedicated, separate space-consuming and flow obstructing ethylene decomposition reactor tank.

Further, according to the invention, existing cooled storing systems such as e.g. reefer containers may be provided with means for decomposition of organic compounds according to the invention. Hereby a very cost-efficient method of obtaining an ethylene decomposition system is provided.

The photo catalytic activity of $TiO_2$ results in thin coatings of the material exhibiting self-cleaning and disinfecting properties under exposure to UV radiation. Thus, a further advantage of the system is that its active surfaces are substantially self-cleaning as mentioned above.

The $TiO_2$ may be in any crystalline form such as in anatase or rutile form. Preferably, it is in the anatase form. This form of $TiO_2$ has particularly high photo catalytic activity.

In one embodiment of the invention, the cooled storing system is a reefer container or a refrigerator. In such systems, the dimensions are often predetermined and standardized. Thus, it is an advantage that the photo catalytic system for decomposition of ethylene is integrated in the surface and does not take up any space, besides for the light tubes arranged in the vicinity of the coated surfaces. Accordingly, the capacity for goods is not influenced by a reactor tank or the like.

In another embodiment, the invention relates to a cooled storing system comprising a storing compartment and a cooling compartment that may be in communication via channels or the like, allowing air to circulate between said compartments, said cooling compartment comprising said cooling unit. Hereby, a system is provided where the cooling unit comprising the means for decomposition of organic compounds such as ethylene is separated from the storing compartment. This may be by provision of some kind of physical barrier such as a wall. Thus, in this embodiment the produce will not come in contact with the coated surfaces and will substantially not be exposed to the UV radiation.

In another embodiment, the invention relates to the cooled storing system according to the above, wherein $TiO_2$ is further provided on one or more additional surfaces of said cooled storing system.

This may be on existing walls or the like or e.g. on a device such as a grid or grating that preferably does not obstruct the airstream, e.g. placed above and/or below the evaporator and arranged so that light emitted from said at least one UV-source falls on said surface provided with $TiO_2$. Hereby, a larger surface area for decomposition of ethylene is provided without reducing the storage capacity and substantially without requiring an increased amount of energy. Further, this allows a higher degree of the UV-emission to be taken advantage of. This means that the system has a greater capacity for decomposition and thus that a higher proportion of the ethylene will be decomposed for each passage of air over the cooling unit.

In one embodiment, the $TiO_2$ is provided on a material selected from the group comprising glass wool, steel wool and rock wool, and wherein said material is provided on said surfaces of the cooled storing system, such as on the evaporator and/or the walls and/or on the above mentioned devices. This further extends the surface area for decomposition as this kind of material has a very large surface area. In a preferred embodiment, $TiO_2$ is provided on a fused quartz product with high silica purity, which is e.g. available from Saint-Gobain as Quartzel®. Because of its purity, this material has the advantage that it does not significantly dim or reduce the UV-light as the light penetrates the material. The material may be applied to the surfaces by any method known to the person skilled in the art. Because of the large surface area of such material, the system thus provided has an even greater capacity for decomposition of organic compounds such as ethylene. Further, as this material is fluffy in nature, it does not in any substantial degree obstruct the airstream, and thus, it preferably does not demand increased energy consumption of the system.

In another embodiment of the invention, the $TiO_2$ is coated directly onto the surfaces. Coating with photo catalytic $TiO_2$ can be performed by several methods including anodizing, sputtering processes, sol-gel chemistry, and from suspension. Coatings may include binders to enhance mechanical stability, co-catalyst or dopants to increase photo catalytic activity or other additives to enhance performance and processability such as wetting-agents. After application of $TiO_2$, post-treatment may be performed such as heat treatment, doping, and activation by irradiation to enhance coating properties.

In another embodiment of the invention, the cooled storing system is only supplied with $TiO_2$ on one or more surfaces of the evaporator. Thus, a very simple and inexpensive system for decomposition is provided.

In another embodiment, the invention relates to a method for cleaning of air and/or surfaces inside a cooled storing system said method comprising photo catalytic decomposition of organic compounds contained in a cooled storing system provided with a cooling unit, said cooling unit comprising an evaporator with at least one surface, said method comprising the steps of:

a) providing an airstream containing organic compounds;
b) providing means for photo catalysis, said means comprising at least one UV-source and $TiO_2$ provided on at least part of said at least one surface of the evaporator, and wherein said at least one UV-source is arranged so that light emitted therefrom falls on said surface provided with $TiO_2$;
c) passing the airstream containing organic compounds over the surface provided with $TiO_2$ and UV light.

According to the invention, a method is provided for cleaning of air and/or surfaces inside a cooled storing system. Particularly, the method is for cleaning of air and/or surfaces for organic compounds. The provision of an airstream in a) may be obtained by any suitable means such as e.g. a fan. Hereby the air may be circulated so that air containing contaminants such as organic compounds can be passed over the surfaces provided with $TiO_2$ and UV light for photo catalytic decomposition of the contaminants. Accordingly, the circulation of air allows for a higher amount of air to be cleaned for organic compounds, because the organic compounds are decomposed by photo catalysis taking place on the active surface as explained above. As explained above, ethylene is undesired in concentrations more than 10 ppbv because it may have an adverse influence on the freshness and stock lifetime of perishable produce like fruit, vegetables as well as flowers and living plants. Accordingly, in one aspect, the invention relates to a method for cleaning the air of organic compounds. In another aspect, the invention relates to a method for decomposition of ethylene contained in a cooled storing system. Accordingly, the air is cleaned by reducing and/or eliminating ethylene from the air.

In another aspect of the invention, the cooled storing system comprises a storing compartment and a cooling compartment containing said cooling unit, said compartments in communication via channels, wherein in step a) the airstream is provided in a direction from the storing compartment to the cooling compartment. The storing compartment is for storing of the produce that may release ethylene or other organic compounds. Accordingly, the air contained in the storing compartment comprising contaminants is to be circulated to the cooling compartment comprising said means for photo catalytic decomposition of said contaminants. The air thus cleaned may re-enter the storing compartment. This may be through communicating channels between said compartments.

The means for photo catalytic decomposition of organic compounds is preferably integrated in the cooling unit and $TiO_2$ is provided on at least part of said at least one surface of the evaporator. As explained above, this provides for a space- and energy-efficient method for decomposition of organic compounds such as ethylene. Another advantage is that organic compounds on the active $TiO_2$ coated surfaces, such as bacteria, are also decomposed by this method.

In one embodiment, the system may be a reefer container or a refrigerator. Such systems are often used for storage of produce such as fruits and plants that emit organic compounds such as e.g. ethylene. Further, such systems are often limited in space and thus it is an advantage that existing surfaces are used as part of the means for cleaning the air.

In a further aspect the invention relates to a method wherein in step b) said $TiO_2$ is further provided on one or more additional surfaces of said cooled storing system. This may be obtained as explained above. Hereby a greater amount of the UV-radiation can be used for photo catalysis and thus, a greater amount of the circulated organic compounds are decomposed.

In one embodiment, the invention relates to a method wherein the $TiO_2$ is in anatase form.

In a further aspect, the invention relates to a method for rendering an existing cooled storing system suitable for decomposition of ethylene and/or organic compounds said system comprising means for providing airflow and a cooling unit, said cooling unit comprising an evaporator with at least one surface, said method comprising the steps of:
providing said existing system with means for photo catalysis, said means comprising at least one UV-source and $TiO_2$ provided on at least part of at least one surface of said evaporator, and wherein said at least one UV-source is arranged so that light emitted therefrom falls on said surface provided with $TiO_2$.

Hereby, a method is provided that enables a very cost-efficient conversion of a cooled storing system that is not ethylene decomposing or where the existing system for ethylene decomposition is space and/or energy-demanding into a system according to the invention, which is both space- and energy-efficient and cost-effective and further, where the active surfaces are substantially self-cleaning when illuminated with UV light.

DESCRIPTION OF THE DRAWING

The invention will be described below, with reference to the accompanying schematic drawing, which for the purpose of illustration shows a non-limiting embodiment and in which FIG. 1 shows a cooled storing system comprising means for photo catalytic decomposition of organic compounds according to the invention.

The FIGURE is not drawn to scale, and only show one embodiment of the invention in order to explain the invention, some parts being omitted and others merely suggested.

In FIG. 1, a cooled storing system (1) comprising a storing compartment (2) and a cooling compartment (3) according to the invention is shown. The storing compartment (2) is shown without its content of produce which may emit ethylene. The cooling compartment (3) is equipped with an evaporator (4) with a surface (5), which evaporator is part of a cooling unit also comprising a condenser and a compressor external to the cooling compartment (not shown). The cooled storing system further contain means for providing an airflow inside said system, such as a fan (6), and one or more UV-sources (7). $TiO_2$ is provided on the surface (5) of the evaporator (4) and may optionally be provided on the surface (8) of a device such as a grid or a rack (9). The UV sources (7) are arranged so that UV light emitted therefrom falls on said surfaces (5 and 8) provided with $TiO_2$ providing for a photo catalytic reaction which leads to decomposition of organic compounds such as ethylene that come into contact with the surface(s).

The storing compartment (2) is in communication with the cooling compartment (3) via channels (10) allowing air to circulate between said compartments. Produce contained in the storing compartment (2) may emit ethylene which is then transported in the airstream (11) to the active surfaces (5 and 8) of the cooling compartment (3) where it is decomposed by photo catalysis. The cleaned air (12) is re-circulated to the storing compartment via channels (10) and ducts (13) in the floor (14) of the cooled storing system (2).

Although the invention above has been described in connection with preferred embodiments of the invention, it will be evident for a person skilled in the art that several modifications are conceivable without departing from the invention as defined by the following claims.

The invention claimed is:

1. A cooled storing system in the form of a reefer container or refrigerator comprising a storing compartment and a cooling compartment in communication via channels through which air circulates between said compartments, said cooling compartment comprising a cooling unit comprising an evaporator and at least one UV-source, wherein $TiO_2$ is provided on a material selected from the group comprising glass wool, rock wool and steel wool and wherein said material is provided on at least part of at least one surface of the evaporator and wherein said at least one UV-source is arranged so that light emitted therefrom falls on said surface provided with $TiO_2$, wherein said cooled reefer or refrigerator further comprises means for providing an airflow inside said reefer or refrigerator, said cooled storing reefer container or refrigerator being adapted to decompose ethylene by a photo catalytic decomposition.

2. The cooled storing reefer container or refrigerator according to claim 1, further comprising at least one device with at least one surface, wherein at least part of the surface of the device is provided with $TiO_2$ and wherein said device is arranged so that light emitted from said at least one UV-source falls on said surface of the device provided with $TiO_2$.

3. The cooled storing reefer container or refrigerator according to claim 1, wherein said $TiO_2$ is coated onto at least one surface of the evaporators.

4. The cooled storing reefer container or refrigerator according to claim 1, wherein said $TiO_2$ is in anatase form.

5. The cooled storing reefer container or refrigerator according to claim 1, wherein said $TiO_2$ is provided in a coating having a thickness of between 10 nm and 300 μm.

6. The cooled storing reefer container or refrigerator according to claim 1, wherein said $TiO_2$ is provided in a coating having a thickness of 1 μm.

7. The cooled storing reefer container or refrigerator according to claim 1, wherein said $TiO_2$ is provided on a fused quartz material, and wherein said fused quartz material is provided on at least part of at least one surface of the evaporator.

8. A method for cleaning of air inside a cooled storing reefer container or refrigerator, said method comprising photo catalytic decomposition of organic compounds comprising ethylene contained in said cooled storing reefer container or refrigerator provided with a cooling unit, said cooling unit comprising an evaporator with at least one surface, said method comprising the steps of:
   a) providing an airstream containing ethylene;
   b) providing means for photo catalysis, said means comprising at least one UV-source and $TiO_2$ is provided on a material selected from the group comprising glass wool, steel wool and rock wool provided on at least part of said at least one surface of the evaporator, and wherein said at least one UV-source is arranged so that light emitted therefrom falls on said surface provided with $TiO_2$;
   c) passing the airstream containing ethylene over the surface provided with $TiO_2$ and UV light.

9. The method according to claim 8, wherein said cooled reefer container or refrigerator further comprises a storing compartment and a cooling compartment containing said cooling unit, wherein said compartments are in communication via channels, wherein in step a) the airstream allows air to circulate between the storing compartment and the cooling compartment.

10. The method according to claim 8, wherein in step b) said $TiO_2$ is further provided on one or more additional surfaces of said cooled storing reefer container or refrigerator.

11. The method according to claim 8, wherein said $TiO_2$ is in anatase form.

12. The method according to claim 8, wherein said air is cleaned by reducing and/or eliminating ethylene from the air.

* * * * *